United States Patent [19]

Kato et al.

[11] 4,115,392
[45] Sep. 19, 1978

[54] MONOFUMARATE SALT OF 3-PYRIDYLMETHYL NICOTINATE

[75] Inventors: Hideo Kato; Eiichi Koshinaka; Sakae Kurata; Ikuo Uesaka, all of Fukui, Japan

[73] Assignee: Hokuriku Pharmaceutical Co., Ltd., Fukui, Japan

[21] Appl. No.: 734,312

[22] Filed: Oct. 20, 1976

[30] Foreign Application Priority Data

Nov. 14, 1975 [DE] Fed. Rep. of Germany ....... 2551283

[51] Int. Cl.$^2$ ............................................ C07D 213/55
[52] U.S. Cl. .............................. 260/295.5 R; 424/266
[58] Field of Search ................................ 260/295.5 R

[56] References Cited

U.S. PATENT DOCUMENTS 2,524,838 10/1950 Sclapfer .................. 260/295.5 R
3,432,510 3/1969 Krimmel .................. 260/295.5 R Primary Examiner—Alan L. Rotman
Attorney, Agent, or Firm—Burgess, Ryan and Wayne

[57] ABSTRACT

The monofumarate of 3-pyridylmethyl nicotinate and the method of making same. The monofumaric acid addition salt of 3-pyridylmethyl nicotinate is prepared by reacting approximately equimolar amounts of fumaric acid and 3-pyridylmethyl nicotinate.

1 Claim, No Drawings

MONOFUMARATE SALT OF 3-PYRIDYLMETHYL NICOTINATE

BACKGROUND OF THE INVENTION

The present invention relates to the monofumarate of 3-pyridylmethyl nicotinate of the following formula:

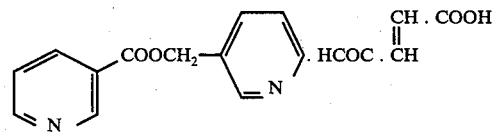

and a process for the preparation thereof. 3-Pyridylmethyl nicotinate and the picrate thereof are already known (Chemical Abstracts 53, 18950K (1959), 54, 1308 g (1960). However, it is difficult to use these compounds as a drug since the ester is in the liquid state at room temperature and unstable. On the other hand, the picrate is toxic and water-insoluble.

It is a primary object of the invention to provide a new monofumarate of 3-pyridylmethyl nicotinate, which is non-hygroscopic, stable and soluble in water, so that it can be used as an anti-hyperlipemic agent having excellent prophylactic and curative effects, and a method of producing the salt.

SUMMARY OF THE INVENTION

According to the present invention the monofumarate of 3-pyridylmethyl nicotinate can be prepared by reacting fumaric acid with 3-pyridylmethyl nicotinate. The salt formation is conducted by treating a solution of fumaric acid in water or in an organic solvent with a solution of 3-pyridylmethyl nicotinate in an equivalent or slightly excess amount with respect to the fumaric acid in the same organic solvent as is used to form the fumaric acid solution. Organic solvents employed in the salt formation are exemplified by the lower alcohols such as methanol, ethanol, isopropanol, butanol and the like.

The acid addition salt can advantageously be formed at room temperature or at a higher temperature, preferably about 20° to 40° C.

The separation of the acid addition salt thus obtained can be carried out in any conventional manner, i.e., by concentrating the reaction solution containing the acid addition salt to crystallize out the salt or by adding an organic solvent, in which the acid addition salt is insoluble or slightly soluble but in which fumaric acid and 3-pyridylmethyl nicotinate are soluble, to the reaction solution. Typical examples of such organic solvents to be used for precipitation are ethyl acetate, ethyl ether, n-hexane, petroleum ether and the like. The monofumarate thus separated can be purified by recrystallization from a lower alcohol as the solvent.

DESCRIPTION OF THE PREFERRED EMBODIMENT

Alternate routes of preparation of the monofumarate of 3-pyridylmethyl-nicotinate according to the invention are shown by the following scheme:

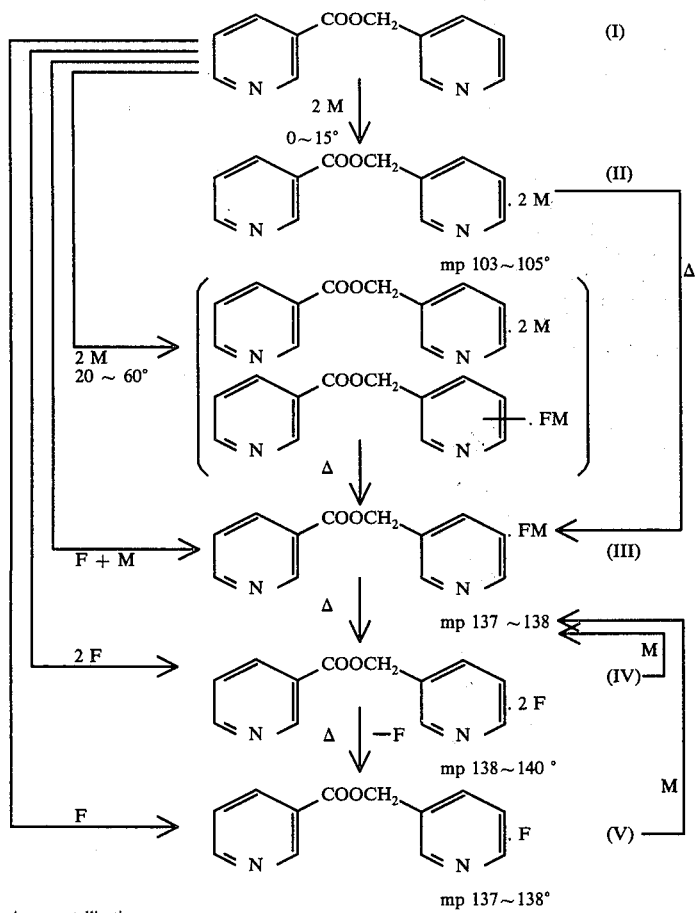

Δ: recrystallization
M: maleic acid
F: fumaric acid

After reaction of 1 mol 3-pyridylmethyl nicotinate base (formula I) with 2 mol maleic acid in water or alcohol under cooling (internal temperature; 0° to 15° C), the dimaleate (formula II) with a melting point of 103° to 105° C is separated out. The dimaleate (Formula II) is recrystallized from water or alcohol in a conventional manner to purify it. During the recrystallization, 1 mol of maleic acid is isomerized to fumaric acid, so that the monomaleate monofumarate (formula III) is formed. The salt of formula III has a melting point of 137° to 138° C. Thin layer chromatography shows a spot of fumaric acid beside the spots of maleic acid and 3-pyridylmethyl nicotinate base (Formula I).

The monomaleate monofumarate (formula III) thus obtained is confirmed by comparison with the acid addition salt which is obtained by the simultaneous reaction of 1 mol maleic acid and 1 mol fumaric acid with the 3-pyridylmethyl nicotinate base.

When the salt formation with 2 mols maleic acid is effected at normal temperature or at higher temperature, preferably at an internal temperature of 20° to 60° C, partial isomerization occurs in the course of the reaction to give a mixture of dimaleate (formula II) with monomaleate monofumarate (formula III). Recrystallization of the mixture gives the monomaleate monofumarate (formula III).

On the other hand, the salt formation of 2 mols fumaric acid with 3-pyridylmethyl nicotinate (formula I) in water results in the difumarate (formula IV) with a melting point of 138° to 140° C, whereas the reaction of 1 or 2 mols fumaric acid in an alcohol results in the monofumarate (formula V) with a melting point of 137° to 138° C.

By recrystallizing the difumarate (formula IV) from an alcohol, 1 mol fumaric acid is eliminated, and the monofumarate (formula V) is separated out.

When the difumarate (formula IV) and monofumarate (formula V) are reacted with 1 mol maleic acid in an alcohol, the monomaleate monofumarate (formula III) is obtained. By recrystallizing the resulting monomaleate monofumarate (formula III) from water or alcohol, the difumarate (formula IV) is obtained after the isomerization of maleic acid to fumaric acid. The isomerization was also proved by disappearance of a spot and signal of maleic acid in the thin layer chromatograph or NMR-spectrum.

Consequently, the difumarate (formula IV) is changed into the monofumarate (formula V) upon eliminating 1 mol fumaric acid as described above.

The structure of the resulting dimaleate (formula II), monomaleate monofumarate (formula III), difumarate (formula IV) and monofumarate (formula V) were confirmed by means of NMR-spectra. The data are summarized in the following table:

As described above, the dimaleate (formula II), monomaleate monofumarate (formula III), difumarate (formula IV) and the monofumarate according to the invention (formula V) may be considered acid addition salts. Surprisingly, the maleic acid isomerized to fumaric acid in the above acid addition salt. It has been found, that the monofumarate is the stablest acid addition salt.

The novel acid addition salt, which is prepared according to the invention, affects the circulatory system and is useful as a vasodilative and antihyperlipemic agent.

The following table shows the increase in blood flow of arteria femoralis after the intraartereal dose in a transfusion experiment of arteria femoralis of anesthesized dogs with a body weight of about 10 kg.

| Doses | 1 mg | 3 mg | 0 mg | 30 mg |
|---|---|---|---|---|
| Compound according to the invention | 25% | 50% | 130% | — |
| Nicotinic acid | — | — | 30% | 70% |

From the above table it can be understood, that the peripheral vasodilative activity of the compound according to the invention is about 10 times stronger than that of nicotinic acid.

The following example illustrates the present invention in greater detail.

EXAMPLE

In 1.3 l methanol, 116 g (1 mol) fumaric acid was dissolved under heating and a solution of 214 g (1 mol) 3-pyridylmethyl nicotinate in 200 ml methanol was dropwise added thereto, so that the internal temperature did not exceed 40° C.

The crystals obtained were filtered and recrystallized twice from methanol to give 180 g monofumarate of 3-pyridylmethyl nicotinate with a melting point of 137° to 138° C.

Analysis for $C_{16}H_{14}O_6N_2$;

| calcd: | C, 58.18: H, 4.27: N, 8.48. |
|---|---|
| found: | C, 58.33: H, 4.26; N, 8.32. |

NMR-spectrum (determined in $D_2O$)

| 0.70 – 2.40 | 8H, m | Hydrogen of pyridine-ring |
|---|---|---|
| 3.30 | 2H, S | Hydrogen of fumaric acid |
| 4.25 | 2H, S | Hydrogen of —COOCH$_2$— |

| compound | Pyridine-ring | Ester —COOCH$_2$— | maleic acid H—C—COO$^-$ ‖ H—C—COOH | fumaric acid H—C—COO$^-$ ⦵ HOOC—CH |
|---|---|---|---|---|
| II | 0.55 – 2.00 (8H, m) | 4.20 (2H,S) | 3.65 (4H,S) | — |
| III | 0.60 – 2.20 (8H, m) | 4.22 (2H,S) | 3.65 (2H,S) | 3.20 (2H,S) |
| IV | 0.60 – 2.20 (8H, m) | 4.25 (2H,S) | — | 3.20 (4H,S) |
| V | 0.70 – 2.40 (8H, m) | 4.25 (2H,S) | — | 3.30 (2H,S) |

S: singlet, m: multiplet

The starting 3-pyridylmethyl nicotinate can be prepared as follows:

109 g (1 mol) of 3-pyridine methanol was dissolved in 200 ml of pyridine and 178 g (1 mol) of nicotinic acid chloride hydrochloride was added thereto in small portions while ice-cooling. After completion of the addition, stirring was conducted for 2 hrs. at room temperature and the reaction mixture was allowed to stand overnight. After pyridine was removed by distillation under reduced pressure, the residue was dissolved in water and rendered alkaline with potassium carbonate and extracted with ether. After the ethereal layer was dehydrated and sodium sulfate, the ether was removed by distillation. Upon distillation of the residue under reduced pressure 3-pyridylmethyl nicotinate was obtained, which had a boiling point of 158° to 164° C/0.5 mmHg.

What is claimed is:
1. Monofumarate of 3-pyridylmethyl nicotinate.
* * * * *

UNITED STATES PATENT OFFICE
CERTIFICATE OF CORRECTION

Patent No. 4,115,392  Dated September 19, 1978

Inventor(s) Hideo Kato, et al

It is certified that error appears in the above-identified patent and that said Letters Patent are hereby corrected as shown below:

Column 2, in the lower part of the reaction scheme, on the right side, under the third benzene ring from the bottom: "138" should be --138°--.

Column 2, in the lower part of the reaction scheme, on the right side, the two arrows shown directed to the 2nd benzene ring from the bottom should be directed to the third benzene ring from the bottom.

Column 4, line 17, in the table: "0 mg" should be --10 mg--.

Column 6, line 2: "and" should be --over--.

Signed and Sealed this

Sixth Day of March 1979

[SEAL]

Attest:

RUTH C. MASON
*Attesting Officer*

DONALD W. BANNER
*Commissioner of Patents and Trademarks*